(12) United States Patent
Hibino

(10) Patent No.: US 9,239,273 B2
(45) Date of Patent: Jan. 19, 2016

(54) SENSOR CONTROL APPARATUS AND SENSOR CONTROL SYSTEM

(71) Applicant: NGK SPARK PLUG CO., LTD., Nagoya-shi, Aichi-ken (JP)

(72) Inventor: Yoshinori Hibino, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 662 days.

(21) Appl. No.: 13/629,451

(22) Filed: Sep. 27, 2012

(65) Prior Publication Data

US 2013/0133399 A1    May 30, 2013

(30) Foreign Application Priority Data

Sep. 29, 2011 (JP) ................................ 2011-215179
Sep. 4, 2012  (JP) ................................ 2012-194220

(51) Int. Cl.

| G01N 27/406 | (2006.01) |
| G01M 15/10  | (2006.01) |
| F02D 41/14  | (2006.01) |
| F02D 41/10  | (2006.01) |

(52) U.S. Cl.
CPC ......... *G01M 15/104* (2013.01); *F02D 41/1446* (2013.01); *F02D 41/1455* (2013.01); *F02D 41/1494* (2013.01); *G01N 27/4065* (2013.01); *G01N 27/4067* (2013.01); *F02D 41/10* (2013.01)

(58) Field of Classification Search
None
See application file for complete search history.

(56) References Cited

U.S. PATENT DOCUMENTS 5,852,228 A    12/1998    Yamashita et al.
5,974,857 A    11/1999    Yamashita et al.

FOREIGN PATENT DOCUMENTS

JP      10-26599 A      1/1998
JP      2003166970   *   6/2003

* cited by examiner

*Primary Examiner* — J. Christopher Ball
(74) *Attorney, Agent, or Firm* — Sughrue Mion, PLLC

(57) ABSTRACT

A CPU (11) of an ECU (5) obtains the present exhaust gas temperature from temperature sensor (3), and calculates the difference with an exhaust gas temperature obtained in a previous computation cycle. When the exhaust gas temperature tends to increase, the absolute value of the difference is equal to or greater than 20° C., and a flag indicating that the processing of correcting a target impedance of a cell (21) of an oxygen sensor (2) is being performed is OFF, the CPU determines that the engine is in a transition period. The CPU then obtains a correction value for the target impedance of the cell of the oxygen sensor on the basis of the exhaust gas temperature. The CPU corrects the target impedance of the cell by the correction value, and feedback-controls electric power supplied to a heater (26) on the basis of the corrected target impedance.

8 Claims, 7 Drawing Sheets

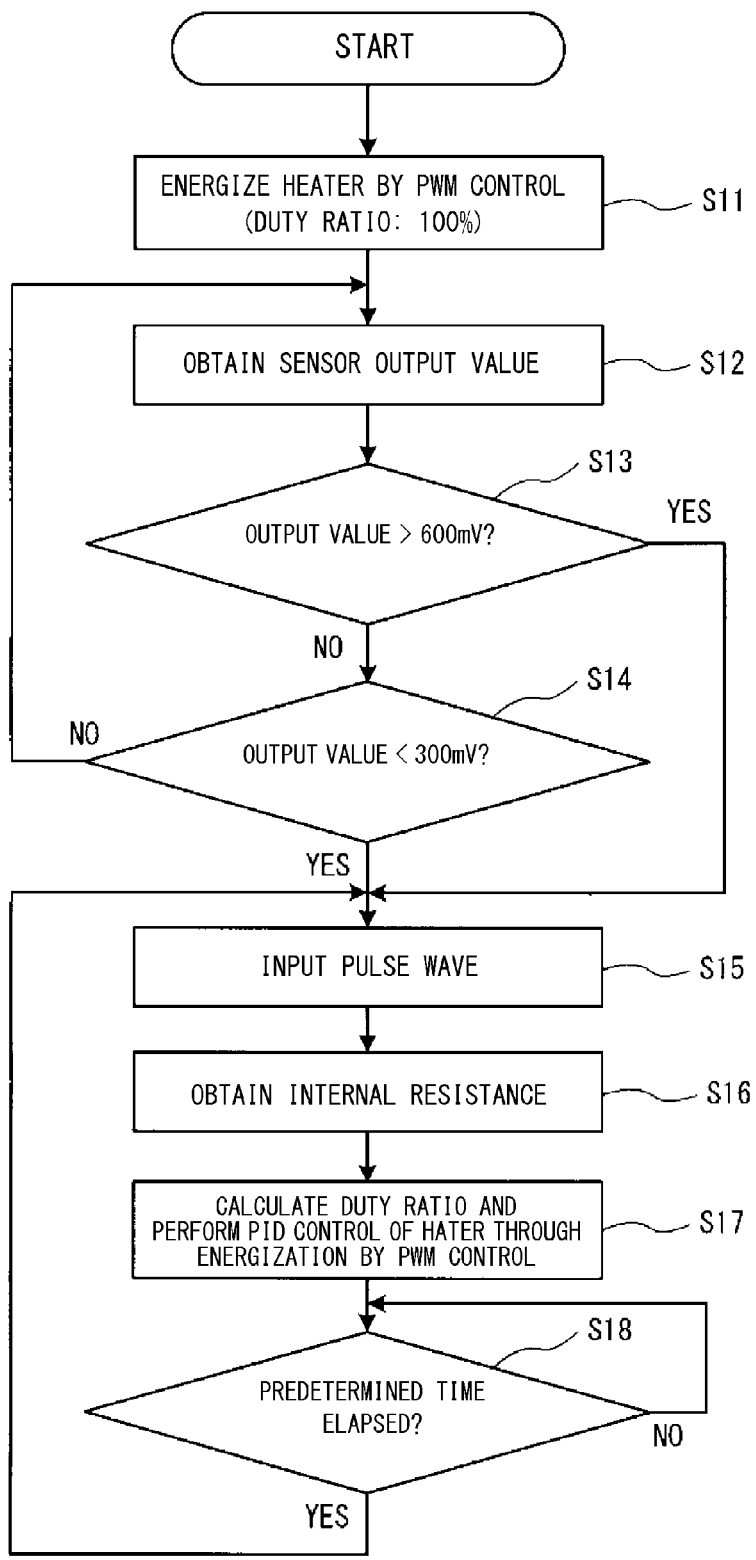

FIG. 5

| | AT THE TIME OF INCREASING | | | | | | |
|---|---|---|---|---|---|---|---|
| EXHAUST GAS TEMPERATURE (°C) | 400 - 500 | 500 - 600 | 600 - 700 | 700 - 720 | 720 - 740 | 740 - 760 | 760 - 800 | 800 - |
| TRANSITION CORRECTION COEFFICIENT | 1.00 | 1.10 | 1.20 | 1.20 | 1.10 | 1.10 | 1.10 | 1.10 |

FIG. 6

| | AT THE TIME OF DECREASING | | | | | | |
|---|---|---|---|---|---|---|---|
| EXHAUST GAS TEMPERATURE (°C) | 400 - 500 | 500 - 600 | 600 - 700 | 700 - 720 | 720 - 740 | 740 - 760 | 760 - 800 | 800 - |
| TRANSITION CORRECTION COEFFICIENT | 1.00 | 1.00 | 0.98 | 0.96 | 0.93 | 0.90 | 0.73 | 0.50 |

SENSOR CONTROL APPARATUS AND SENSOR CONTROL SYSTEM

TECHNICAL FIELD

The present invention relates to a sensor control apparatus for controlling a gas sensor which detects the concentration of a specific gas contained in exhaust gas exhausted from an internal combustion engine, and to a sensor control system which includes the gas sensor and the sensor control apparatus connected thereto.

BACKGROUND ART

Conventionally, a gas sensor is disposed in an exhaust passage (exhaust pipe) of an internal combustion engine of an automobile or the like, and the air-fuel ratio is controlled by detecting the concentration of a specific gas contained in exhaust gas through use of the gas sensor. Specific examples of such gas sensor are an oxygen sensor for detecting the oxygen concentration of exhaust gas and an NOx sensor for detecting the concentration of nitrogen oxide (NOx). Such an oxygen sensor includes a detection element having at least one cell composed of an oxygen-ion conductive solid electrolyte member and a pair of electrodes formed thereon. Since the cell formed of a solid electrolyte member exhibits good oxygen ion conductivity when it is heated to a predetermined temperature (activation temperature), a heater for heating the detection element is provided. In order to maintain the active state of the oxygen sensor (cell), the temperature of the detection element is fed back to a controller so as to control the electric power supplied to the heater for heating the detection element (element temperature feedback control). This element temperature feedback control is performed on the basis of the impedance of the detection element which changes with the temperature thereof. At that time, an impedance corresponding to the activation temperature is used as a target impedance. However, when the oxygen sensor deteriorates, the impedance of the detection element increases. In such a case, even when the temperature of the oxygen sensor is the activation temperature, due to the increased impedance of the detection element, the electric power supplied to the heater is increased such that the detection element has the target impedance. As a result, the temperature of the oxygen sensor increases. This temperature increase raises a problem of accelerating the deterioration of the oxygen sensor.

In order to solve such a problem, there has been proposed an oxygen concentration detection apparatus which includes heater-supplied-power control means for feedback-controlling the electric power supplied to the heater such that the impedance of the detection element, which changes with the temperature thereof, becomes a target impedance; deterioration determination means for determining whether or not the oxygen sensor has deteriorated on the bases of an increase in the impedance of the detection element; and target impedance change means for changing the target impedance to increase when the oxygen sensor is determined to have deteriorated (see, for example, Patent Document 1). When the oxygen sensor has deteriorated, the electric power supplied to the heater is controlled by changing the target impedance to a new target impedance, to thereby prevent the temperature of the oxygen sensor from increasing. Thus, the oxygen sensor can be maintained at a target element temperature.

[Patent Document 1] Japanese Patent Application Laid-Open (kokai) No H10-26599

DISCLOSURE OF THE INVENTION

Problem to be Solved by the Invention

Incidentally, in a transition period in which the operation state of an internal combustion engine changes suddenly, the temperature of exhaust gas flowing through the exhaust pipe changes greatly. At that time, the temperature of exhaust gas around the oxygen sensor also changes greatly. Since the influence of the temperature change of the exhaust gas on the impedance of the detection element is relatively large, even when the electric power supplied to the heater is feedback-controlled such that the detection element has a fixed (constant) target impedance, the impedance of the detection element cannot be controlled (maintained) at the target element temperature. Although the oxygen concentration detection apparatus disclosed in Patent Document 1 corrects the target impedance, the correction is performed in consideration of the deterioration of the oxygen sensor only, and the target impedance is not corrected in consideration of the transition period in which the operation state of the internal combustion engine changes suddenly.

An object of the present invention is to provide a sensor control apparatus and a sensor control system which can accurately control a gas sensor to a target element temperature even in a transition period in which the operation state of an internal combustion engine changes.

Means for Solving the Problems

One mode of the present invention which solves the above-described problem is a sensor control apparatus connected to a gas sensor which is attached to an exhaust pipe of an internal combustion engine and which includes a detection element for detecting the concentration of a gas contained in exhaust gas and a heater for heating the detection element. The sensor control apparatus comprises element impedance detection means for detecting an impedance of the detection element; heater-supplied-power control means for feedback-controlling power supplied to the heater such that the element impedance detected by the element impedance detection means coincides with a target impedance; temperature change determination means for determining whether or not a change in the temperature of exhaust gas flowing through the exhaust pipe falls outside a previously set allowable range; and correction means for correcting the target impedance when the temperature change determination means determines that the change in the temperature of the exhaust gas falls outside the allowable range.

In a transition period in which the operation state of the internal combustion engine changes suddenly, the temperature of the exhaust gas also changes suddenly. In consideration of this phenomenon, in the sensor control apparatus having the above-described configuration, the temperature change determination means determines whether or not a change in the temperature of the exhaust gas falls outside the specific range, and the target impedance is corrected when the temperature change determination means determines that the change in the temperature of the exhaust gas falls outside the specific range. Therefore, even when the impedance of the detection element is affected by a large temperature change of the exhaust gas, the detection element can be controlled to a target element temperature through use of the heater-supplied-power control means.

Notably, the temperature change determination means may be configured to determine whether or not the change in the temperature of the exhaust gas detected through use of means for directly detecting the temperature of the exhaust gas (e.g., an exhaust gas temperature sensor) falls outside the allowable range. Alternatively, the temperature change determination means may be configured to determine whether or not the change in the temperature of the exhaust gas estimated on the basis of the operation state of the internal combustion engine falls outside the allowable range.

In the sensor control apparatus of the present invention, the correction means may be configured to correct the target impedance by multiplying the target impedance by a correction coefficient, and change the correction coefficient on the basis of the temperature of the exhaust gas at the time of start of a change in the temperature of the exhaust gas, which change has deviated from the allowable range. Even when the amount of change in the exhaust gas temperature per unit time is the same among different states, if the temperature at the time of start of the change differs among the different states, the influence on the impedance of the detection element also differs amount the different states. In consideration of this, the correction coefficient used for correcting the target impedance is changed on the basis of the temperature of the exhaust gas at the time of start of a change in the temperature of the exhaust gas, which change has deviated from the allowable range. Thus, an accurate correction coefficient for the target impedance can be calculated.

In the sensor control apparatus of the present invention, the temperature change determination means may be configured to determine whether or not the change in the temperature of the exhaust gas falls outside the allowable range by determining whether or not a change in an output value of an exhaust gas temperature sensor attached to the exhaust pipe and detecting the temperature of the exhaust gas falls outside a specific range. When the change in the temperature of the exhaust gas is determined whether or not it falls outside the allowable range, the change in the temperature of the exhaust gas can be detected directly through utilization of the output of the exhaust gas temperature sensor. Therefore, it is possible to accurately determine whether or not the internal combustion engine is in a transition period in which the operation state of the internal combustion engine changes suddenly, and to accurately perform the correction of the target impedance. Notably, the size of the specific range is set in accordance with the allowable range such that, when the change in the output value of the exhaust gas temperature sensor deviates from the specific range, the change in the temperature of the exhaust gas also deviates from the allowable range.

In the sensor control apparatus of the present invention, the specific range may be determined in consideration of the sampling timing of the output value of the exhaust gas temperature sensor, etc. such that it becomes possible to detect that the internal combustion engine to which the gas sensor is attached is in a transition period during which its operation state changes. For example, the specific range may be the range of a change in the output value corresponding to 10° C. or greater per sec. A period during which the temperature of the exhaust gas changes 10° C. or greater per sec can be considered a transition period in which the operation state of the internal combustion engine changes suddenly. Therefore, by using such a range as the specific range, it is possible to effectively perform the correction of the target impedance in consideration of the transition period in which the operation state of the internal combustion engine changes.

The sensor control apparatus of the present invention may further comprise time determination means for determining whether or not a state in which the difference between output values of the exhaust gas temperature sensor obtained at predetermined time intervals is equal to or lower than a predetermined value has continued for a predetermined period of time, wherein the correction means stops the correction of the target impedance when the time determination means determines that the state in which the difference between output values of the exhaust gas temperature sensor obtained at the predetermined time intervals is equal to or lower than the predetermined value has continued for the predetermined period of time. In the case where the state in which the temperature change per unit time falls within the predetermined range has continued for a predetermined period of time, the operation state of the internal combustion engine is not transitional anymore. Therefore, the target impedance is not required to be corrected, and only thing that is required is feedback-controlling the electric power supplied to the heater while returning the target impedance to the original target impedance.

The correction means may be configured to correct the target impedance when the output value of the exhaust gas temperature sensor indicates that the temperature of the exhaust gas is increasing and the temperature change determination means determines that the change in the output value falls outside the specific range. The correction of the target impedance changes depending on whether the temperature of the exhaust gas is increasing or decreasing. Accordingly, in the case where the temperature of the exhaust gas is increasing, the correction of the target impedance suitable for such a state can be performed.

Also, the correction means may be configured to correct the target impedance when the output value of the exhaust gas temperature sensor indicates that the temperature of the exhaust gas is decreasing and the temperature change determination means determines that the change in the output value falls outside the specific range. Accordingly, in the case where the temperature of the exhaust gas is decreasing, the correction of the target impedance suitable for such a state can be performed.

Another mode of the present invention which solves the above-described problem is a sensor control system comprising the gas sensor and the above-described sensor control apparatus connected to the gas sensor. Thus, it becomes possible to provide a sensor control system which can control the detection element to the target element temperature through use of the heater-supplied-power control means even when the impedance of the detection element is affected by a large temperature change of the exhaust gas.

EFFECT OF THE INVENTION

The present invention provides the following effects. In a transition period in which the operation state of the internal combustion engine changes suddenly, the temperature of the exhaust gas also changes suddenly. In consideration of this phenomenon, the temperature change determination means determines whether or not a change in the temperature of the exhaust gas falls outside the allowable range, and the target impedance is corrected when the temperature change determination means determines that the change in the temperature of the exhaust gas falls outside the allowable range. Therefore, it is possible to perform accurate correction of the target impedance suitable for the transition period in which the operation state of the internal combustion engine changes suddenly. Accordingly, even in the case where the operation state of the internal combustion engine is transitional, the gas sensor (detection element) can be controlled (maintained) at a target (constant) element temperature, whereby the detection accuracy of the gas sensor can be maintained well during the operation period of the internal combustion engine.

BRIEF DESCRIPTION OF THE DRAWINGS

[FIG. 3] Flowchart of main processing.

[FIG. 5] Table showing the correspondence between exhaust gas temperature and correction coefficient employed when exhaust gas temperature increases.

[FIG. 6] Table showing the correspondence between exhaust gas temperature and correction coefficient employed when exhaust gas temperature decreases.

MODE FOR CARRYING OUT THE INVENTION

An electronic control unit (hereinafter referred to as the "ECU") 5, which is one embodiment of the sensor control apparatus of the present invention, and a gas sensor apparatus 1 including the ECU 5 will now be described with reference to the drawings. Notably, the drawings which will be referred to are used to describe technical features which the present invention can employ, and the structure, etc. of the described apparatus do not limit the present invention and are mere explanatory examples.

Figure 1:
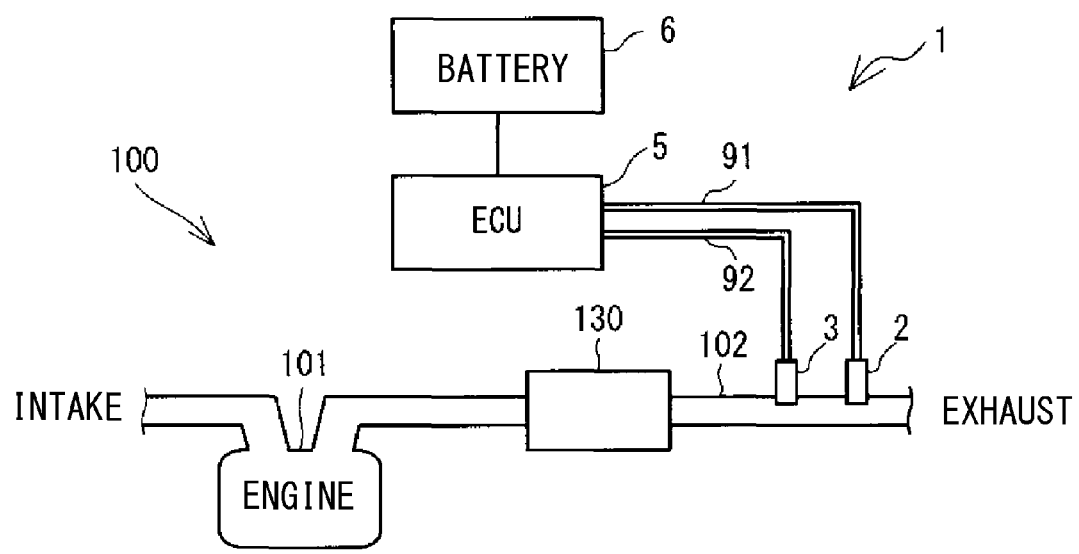
[FIG. 1] Diagram schematically showing the configuration of an exhaust system of an engine 101.

As shown in FIG. 1, an automobile 100 includes an engine 101 for producing drive power, and the ECU 5 for controlling the operation (operation state) of the engine 101. An exhaust pipe 102 is connected to the engine 101 so as to discharge, to the outside of the automobile, exhaust gas exhausted from the engine 101. An exhaust gas purifying unit 130 is provided in the exhaust pipe 102, and an exhaust gas temperature sensor 3 for detecting the temperature of the exhaust gas and an oxygen sensor 2 for detecting the concentration of oxygen contained in the exhaust gas are provided downstream of the exhaust gas purifying unit 130. The oxygen sensor 2 is electrically connected to an offset circuit 40 (see FIG. 2) of the ECU 5 through a harness 91, and the exhaust gas temperature sensor 3 is connected to the ECU 5 through a harness 92. The gas sensor apparatus 1 is composed of the ECU 5, the oxygen sensor 2, and the exhaust gas temperature sensor 3.

Figure 2:
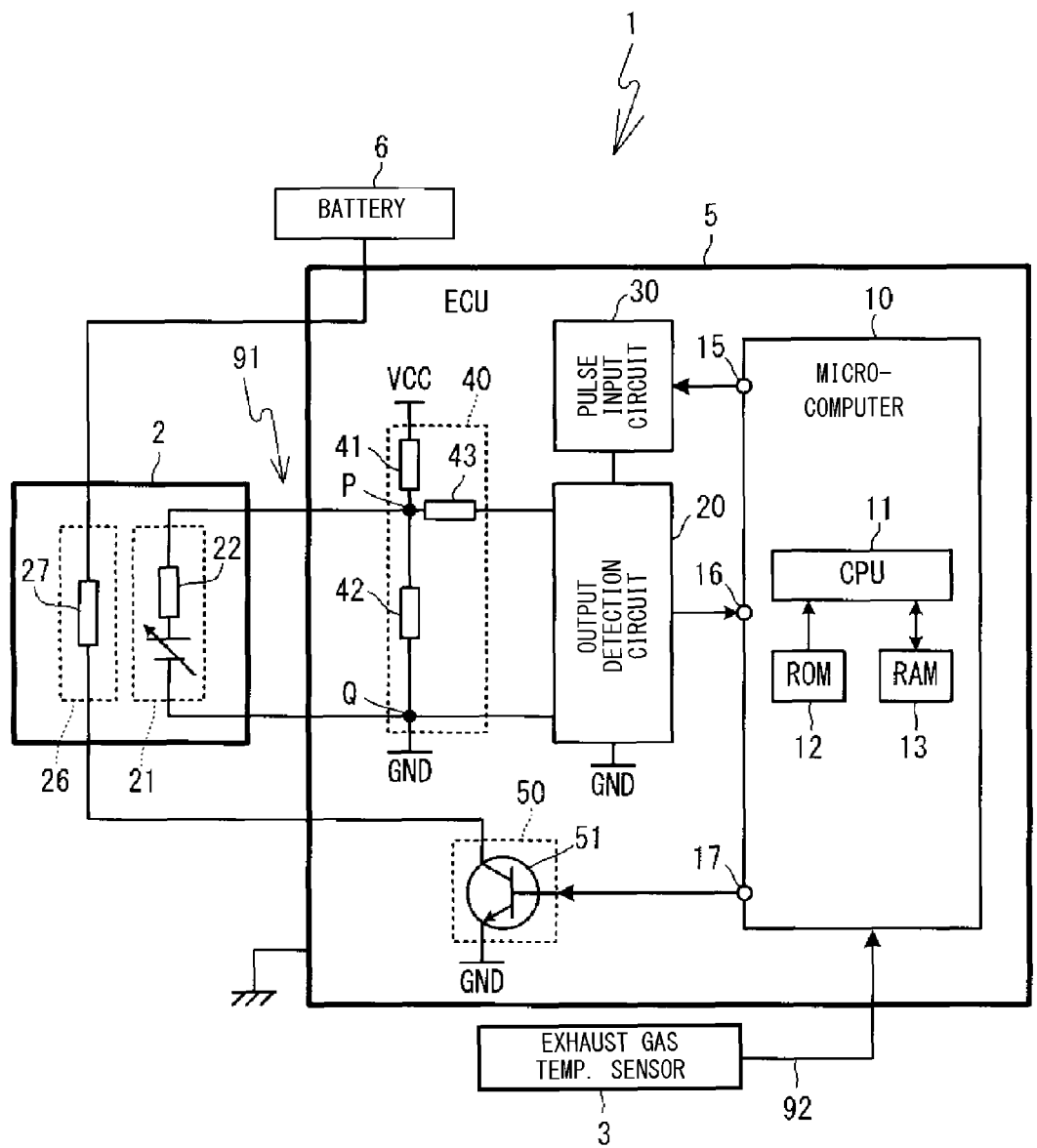
[FIG. 2] Explanatory view schematically showing the configurations of an ECU 5, an oxygen sensor 2, and an exhaust gas temperature sensor 3.

The oxygen sensor 2 shown in FIG. 2 has a structure in which a heater 26 is inserted into a sensor element which is formed into a bottomed tubular shape through use of a single cell 21, and the sensor element is held inside a metallic shell which is attached to an exhaust pipe (not shown). The heater 26, which is formed into a barlike or platelike shape, includes a heating resistor 27, which is mainly formed of platinum, tungsten, or the like and which is buried in a base member formed of insulating ceramic of alumina. When the oxygen sensor 2 is attached to the exhaust pipe, a distal end portion of the bottomed-tubular sensor element (located on the side toward the bottom of the tube) is inserted into the exhaust pipe so that one porous electrode of the cell 21 (the electrode formed on the outer circumference of the sensor element) is exposed to exhaust gas. The other porous electrode of the cell 21 (the electrode formed on the inner circumference of the sensor element) is exposed to a reference gas (air in the present embodiment) introduced into the tube from the outside of the exhaust pipe. Thus, as described above, the air-fuel ratio of the exhaust gas (the oxygen concentration of the exhaust gas) is detected.

The cell 21 has an internal resister 22. It has been known that the resistance (impedance) of the internal resistor 22 decreases as the temperature of the solid electrolyte member increases, and has a predetermined correlation with the temperature of the cell 21. In the gas sensor apparatus 1, the internal resistance (impedance) of the cell 21 is detected, and the electric power supplied to the heater 26 is controlled such that the internal resistance coincides with a target resistance. Thus, the temperature of the cell 21 is stabilized such that the temperature of the cell 21 is maintained at a target element temperature.

The ECU 5 is an apparatus for performing control of the engine 101, including air-fuel-ratio feedback control (e.g., adjustment of the amount of fuel injected from an injector), on the basis of the detection signal output from the oxygen sensor 2. In the present embodiment, there will be described the configuration of the ECU 5 required to accurately perform PID control for the heater 26, and to detect the internal resistance (impedance) of the cell 21 on the basis of the detection signal output from the oxygen sensor 2. The ECU 5 includes a microcomputer 10, an output detection circuit 20, a pulse input circuit 30, an offset circuit 40, and a heater control circuit 50. The microcomputer 10 includes a CPU 11 which governs the control of the ECU 5; ROM 12 which stores programs to be executed by the CPU 11, etc.; RAM 13 which temporarily stores various data; and input and output ports 15, 16, 17, etc. for receiving and outputting signals. Notably, the CPU 11, ROM 12, and RAM 13 of the microcomputer 10 have known configurations. Also, the exhaust gas temperature sensor 3 is connected to the microcomputer 10 via an unillustrated interface, and data representing the temperature detected by the exhaust gas temperature sensor 3 is input to the microcomputer 10.

The output detection circuit 20, which is a known circuit including resistors, etc., is electrically connected to opposite ends of the cell 21 of the oxygen sensor 2; that is, the two porous electrodes, via the offset circuit 40. The detection signal output from the cell 21 is input to the output detection circuit 20, whereby a potential difference between the opposite ends of the cell 21 is detected. The electromotive force generated in the cell 21 can be detected from the potential difference between the opposite ends of the cell 21. The output detection circuit 20 obtains (detects) the potential difference between the opposite ends of the cell 21 at predetermined intervals, and outputs it to the A/D port 16 of the microcomputer 10 as a signal representing the electromotive force of the cell 21.

Also, the output detection circuit 20 has an unillustrated sample hold circuit, and can hold the obtained potential difference between the opposite ends of the cell 21. When a pulse voltage is applied to the cell 21, the potential difference between the opposite ends changes in accordance with the internal resistance of the cell 21. Therefore, when the internal resistance (impedance) of the cell 21 is to be detected, a pulse voltage is applied to the cell 21 by the pulse input circuit 30. The output detection circuit 20 also detects the potential difference between the opposite ends of the cell 21 when the pulse voltage is applied to the cell 21. At that time, the potential difference between the opposite ends of the cell 21 immediately before the application of the pulse voltage is held in the sample hold circuit. The output detection circuit 20 outputs to the A/D port 16 of the microcomputer 10 the difference between the potential difference in the case where the pulse voltage is not applied and that in the case where the pulse voltage is applied; that is, a change in the potential difference caused by the application of the pulse voltage, as a signal representing the internal resistance of the cell 21.

The offset circuit 40 is provided in wiring lines which connect the opposite ends of the cell 21 to the output detection circuit 20, and offsets the potential of the electromotive force output from the cell 21. Specifically, a resistor 42 is connected to a node P on a wiring line which establishes connection between the higher-potential side end of the cell 21 and the output detection circuit 20 and to a node Q on a wiring line which establishes connection between the lower-potential side end of the cell 21 and the output detection circuit 20. The node Q on the lower potential side is connected to a reference potential line (GND) of the ECU 5. Notably, the reference potential line of the ECU 5 is connected to, for example, the body of the automobile. The node P on the higher potential side is connected, via a resistor 41, to a power supply which outputs a predetermined power supply voltage VCC. Also, a resistor 43 for noise prevention is connected between the node P and the output detection circuit 20.

As described above, the solid electrolyte member, which partially constitutes the cell 21, has a characteristic such that its internal resistance (impedance) decreases as the temperature of the solid electrolyte member increases. That is, in a state in which the temperature of the solid electrolyte member is low (hereinafter may be referred to a "non-active state"), the internal resistance is high, and the cell 21 substantially becomes insulative. Also, as the temperature of the solid electrolyte member increases, the internal resistance decreases. When the cell 21 is activated (hereinafter may be referred to as an "active state"), the internal resistance is low. When the air-fuel ratio of the exhaust gas is on the rich side, the electromotive force of the cell 21 has a potential difference of about 900 mV in relation to the reference potential. When the air-fuel ratio of the exhaust gas is on the lean side, the electromotive force of the cell 21 has a potential difference of about 50 mV in relation to the reference potential.

The power supply voltage VCC is divided by the resistor 41 and the resistor 42 such that the potential at the node P becomes about 450 mV in the present embodiment. The resistor 42 is selected such that its resistance is sufficiently smaller than the internal resistance of the cell 21 in the non-active state, and is sufficiently lager than the internal resistance of the cell 21 in the active state. When the cell 21 is in the non-active state, no current flows through the cell 21, and no electromotive force is generated. Therefore, the output of the cell 21 is 0 V. However, the output detection circuit 20 receives about 450 mV from the offset circuit 40 as the output of the cell 21. Meanwhile, when the cell 21 is in the active state, current hardly flows through the resistor 42 whose resistance is sufficiently larger than the internal resistance. Therefore, the voltage which the output detection circuit 20 receives from the offset circuit 40 as the output value of the cell 21 (the value indicated by the detection signal) is substantially equal to the electromotive force of the cell 21.

The heater control circuit 50 includes a transistor 51, for example. The collector of the transistor 51 is connected to one end of the heater 26, the emitter of the transistor 51 is connected to the reference potential line via a predetermined resistor (not shown), and the base of the transistor 51 is connected to the PWM port 17 of the microcomputer 10. The other end of the heater 26 is connected to a battery 6, which supplies electric power to the ECU 5. The energization of the heater 26 is controlled by the microcomputer 10 through PID control. Electricity is supplied from the heater control circuit 50 to the heater 26 through PWM control performed on the basis of a duty ratio computed by the microcomputer 10. Specifically, a signal for turning the transistor 51 on and off is output from the PWM port 17 of the microcomputer 10 so as to control the current flowing between the collector and emitter of the transistor 51; that is, the current flowing from the battery 6 to the heater 26. Notably, the heater control circuit 50 may be configured through use of an FET or the like instead of the transistor 51.

The pulse input circuit 30 is a circuit for applying a pulse voltage having a rectangular waveform to the cell 21 via the output detection circuit 20. Digital data representing a rectangular pulse waveform are generated through computation performed by the microcomputer 10, and are output from the I/O port 15 to the pulse input circuit 30. The pulse input circuit 30 generates a rectangular pulse voltage on the basis of the received pulse waveform data, and applies the pulse voltage to the cell 21. Notably, the application time of the pulse voltage can be properly determined within a range of several ms to several hundreds of ms.

As described above, as a result of application of the pulse voltage to the cell 21, the potential difference between the opposite ends of the cell 21, which is acquired (detected) by the output detection circuit 20, changes temporarily. In other words, the potential generated between the opposite ends of the internal resistor 22 as a result of application of the pulse voltage is added to the electromotive force of the cell 21, and the sum of the potential and the electromotive force is acquired (detected) by the output detection circuit 20 as the detection signal output from the cell 21. Therefore, the internal resistance of the cell 21 (thus, the temperature of the cell 21, which has a correlation with the internal resistance) can be computed from the change in the potential difference between the opposite ends of the cell 21, which change is produced as a result of application of the pulse voltage and is obtained by the output detection circuit 20 as a detection signal. In the gas sensor apparatus 1, when the cell 21 is in the active state, electric power is supplied to the heater 26 through PWM control based on PID control, as described above, such that the internal resistance (impedance) of the cell 21 coincides with the target impedance.

Next, the main processing of the gas sensor apparatus 1 will be described. Notably, in the following description, each step in the flowchart is abbreviated to "S."

The gas sensor apparatus 1 is powered, for example, when the engine of the automobile is started, and the CPU 11 of the microcomputer 10 of the ECU 5 starts the execution of a main processing program stored in the ROM 12. As shown in FIG. 3, the CPU 11, which has started the main processing program, sets a duty ratio used in the PWM control to a fixed value (S11). Notably, in the present embodiment, this duty ratio is set to 1 (100%), and a continuous ON/OFF signal is output to the heater control circuit 50 (in this case, an normally ON signal is output to the heater control circuit 50). The voltage of the battery 6 is applied to the heating resistor 27 of the heater 26 as it is, whereby the temperature of the cell 21 increases with time.

Next, the CPU 11 obtains the output (detection signal) of the gas sensor 2 (S12). In this processing, the detection signal of the cell 21 obtained via the output detection circuit 20 is input to the microcomputer 10 via the A/D port 16, and the CPU 11 reads the value of the detection signal (S12). As long as the value (voltage) of the detection signal is not higher than 600 mV (S13: NO) and is not lower than 300 mV (S14: NO), the CPU 11 returns to S12 so as to repeat the monitoring of the value of the detection signal. When the cell 21 is in a non-active state (a state before the temperature of the cell 21 reaches the activation temperature), the voltage of the detection signal is about 450 mV. Even after the temperature of the cell 21 has reached the activation temperature, the voltage of the detection signal becomes 600 mV or lower when the air-fuel ratio is on the rich side and becomes 300 mV or higher when the air-fuel ratio is on the lean side, in a period in which the cell 21 has not yet been heated sufficiently. In such a case, despite that the cell 21 is activated, the difference between the value of the detection signal when the air-fuel ratio of the exhaust gas is on the rich side and the value of the detection signal when the air-fuel ratio of the exhaust gas is on the lean side is small, and the accuracy required for detecting the air-fuel ratio of the exhaust gas cannot be obtained satisfactorily.

In the case where the output (output voltage) of the cell 21 becomes higher than 600 mV when the air-fuel ratio of the exhaust gas changes to the rich side (S13: YES) or in the case where the output (output voltage) of the cell 21 becomes lower than 300 mV when the air-fuel ratio of the exhaust gas changes to the rich side (S14: YES), the CPU 11 proceeds to S15. Since the engine has already been started, the air-fuel ratio of the exhaust gas changes momentarily. If the output value of the cell 21 becomes greater than 600 mV or smaller than 300 mV, the cell 21 is determined to have been activated to a degree required for obtaining a necessary accuracy for detection of the air-fuel ratio of the exhaust gas. As a result, the ECU 5 can change the separately performed air-fuel-ratio open loop control to the known air-fuel-ratio feedback control (closed loop control of the air-fuel ratio) performed on the basis of the output (detection signal) of the cell 21.

The CPU 11 outputs digital data representing a pulse waveform to the pulse input circuit 30 via the I/O port 15 (S15). The pulse input circuit 30 generates a rectangular pulse voltage, and applies the pulse voltage to the cell 21. The output detection circuit 20 obtains the potential of the cell 21 having changed as a result of application of the pulse voltage, and outputs it to the A/D port 16 of the microcomputer 10. The CPU 11 computes the present internal resistance (impedance) of the cell 21 from the obtained potential of the cell 21 having changed as a result of application of the pulse voltage (S16).

The CPU 11 performs PID computation on the basis of the internal resistance (impedance) of the cell 21 obtained in S16 and a target impedance TRi, and calculates the duty ratio used for controlling the supply of electricity to the heater 26 through PWM control. Notably, the above-mentioned PID computation is realized by executing a known computation routine. Then, the CPU 11 continuously outputs an ON/OFF signal to the heater control circuit 50 (S17) in accordance with the calculated duty ratio. That is, by means of the heater control program (not shown), a PMW control signal for turning the transistor 51 on and off in accordance with the duty ratio is generated, and is output to the heater control circuit 50. Notably, the target impedance TRi, which is used for PID computation in S17, is the latest (in other words, corrected) target impedance TRi. Every time the processing of S17 is executed, the latest target impedance TRi is obtained by multiplying a previously set target impedance TRi by a transition correction coefficient to be described later. Calculation of the transition correction coefficient and correction of the target impedance TRi will be described later.

Next, the CPU 11 waits for elapse of a predetermined time (e.g., 10 to 50 msec) (S18: NO). When the CPU 11 determines that the predetermined time has elapsed (S18: YES), the CPU 11 applies the pulse voltage to the cell 21 (S15). Subsequently, the CPU 11 repeats S16 to S18.

Figure 4A:
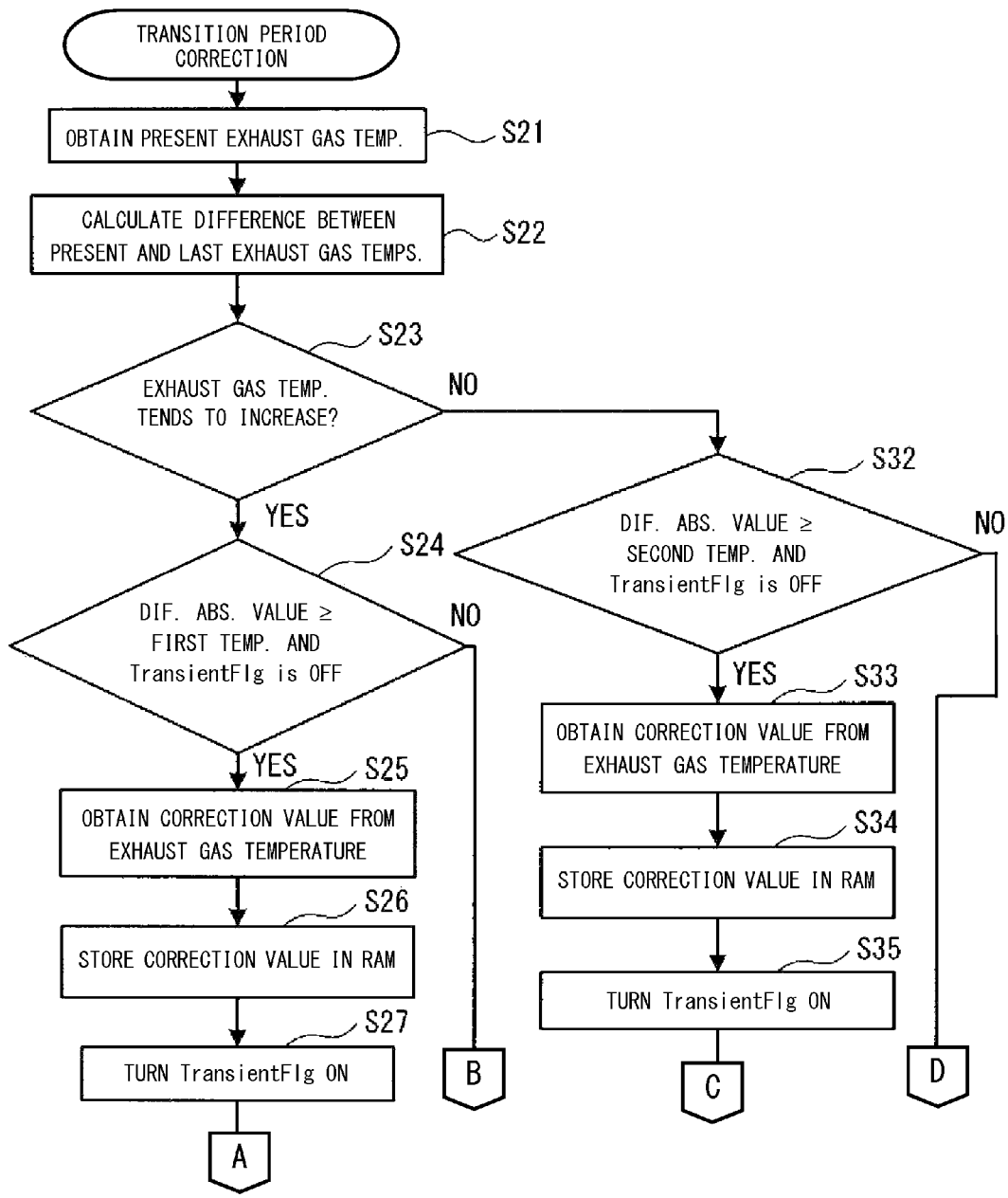
[FIG. 4(A)] and [FIG. 4(B)] together show a flowchart of transition period correction processing, where FIG. 4(B) continues from FIG. 4(A) at junction points A, B, C and D.
Figure 4B:
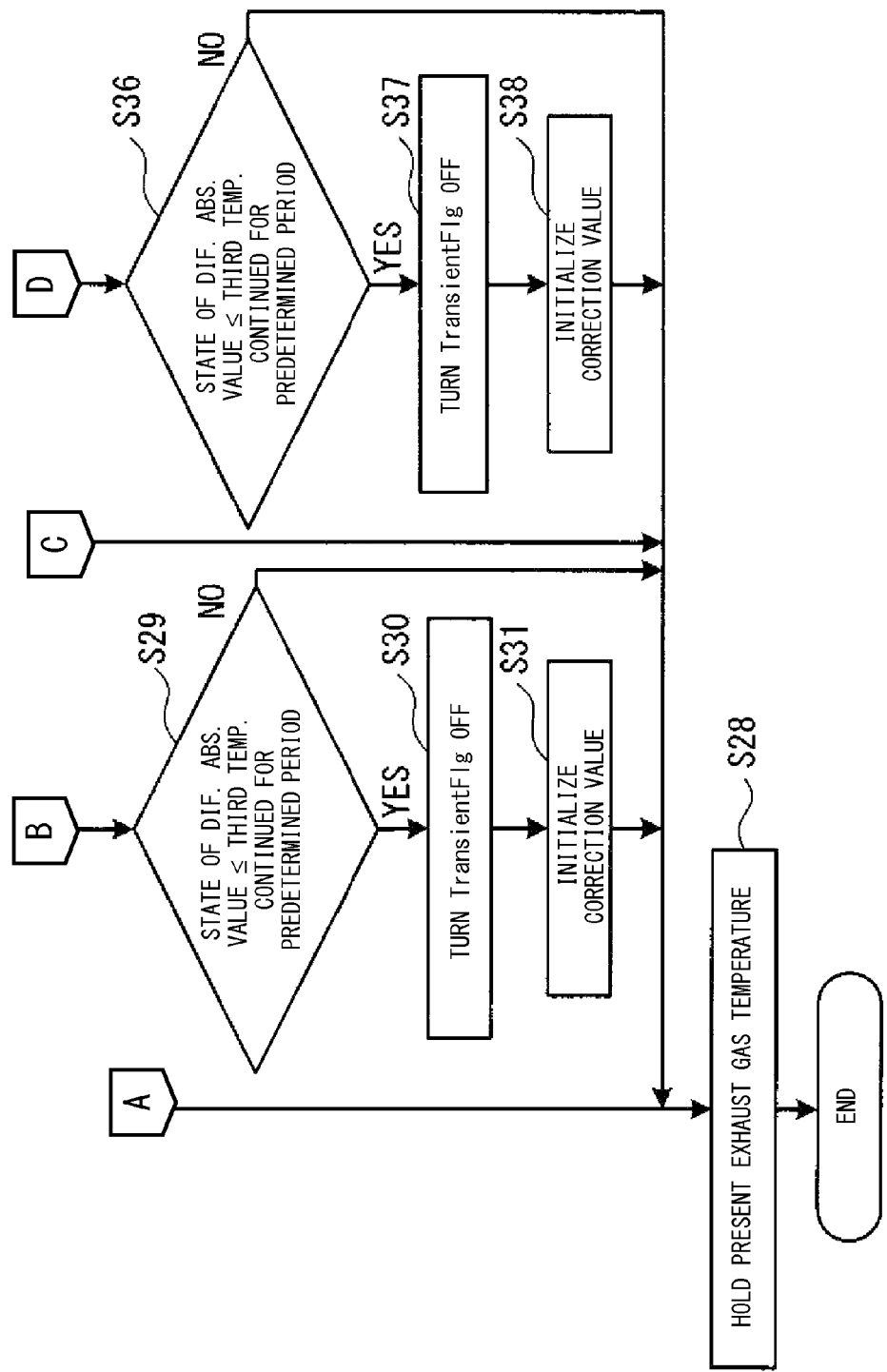

Next, a transition period correction of the target impedance which is performed during a transition period of operation of the engine 101 will be described with reference to the flowchart of FIG. 4(A) and FIG. 4(B). A transition period correction program of the flowchart of FIG. 4(A) and FIG. 4(B) is stored in the ROM 12, and is repeatedly executed by the CPU 11 every time 1 second elapses. The CPU 11 first obtains the present exhaust gas temperature from the exhaust gas temperature sensor 3 (S21). Subsequently, the CPU 11 calculates the difference between the present exhaust gas temperature and the last exhaust gas temperature already stored in the RAM 13 (S22). This difference is also stored in the RAM 13. Next, the CPU 11 determines whether or not the exhaust gas temperature tends to increase (S23). The CPU 11 determines that the exhaust gas temperature tends to increase (S23: YES) when the difference calculated in S22 is positive, and determines that the exhaust gas temperature does not tend to increase (S23: NO) when the difference calculated in S22 is zero or negative.

In the case where the exhaust gas temperature tends to increase (S23: YES), the CPU 11 determines whether or not the absolute value of the difference is not less than a first temperature (e.g., 20° C.) and a TransientFlg is OFF. This TransientFlg is a flag indicating whether the transition period correction is being performed, and is stored in the RAM 13. When the value of the TransientFlg is "1," the TransientFlg is ON, and when the value of the TransientFlg is "0," the TransientFlg is OFF. In the case where the absolute value of the difference is not less than the first temperature and the TransientFlg is OFF (S24: YES), with reference to a correction coefficient table which is shown in FIG. 5 and which is used when the exhaust gas temperature increases, the CPU 11 obtains a correction coefficient for the target impedance transition, which coefficient corresponds to the present exhaust gas temperature obtained in S21 (S25). This correction coefficient table which is used when the exhaust gas temperature increases is stored in the ROM 12. For example, when the exhaust gas temperature obtained from the exhaust gas temperature sensor 3 is not lower than 400° C. and lower than 500° C., 1.00 is obtained as the transition correction coefficient. When the obtained exhaust gas temperature is not lower than 500° C. and lower than 600° C., 1.10 is obtained as the transition correction coefficient. When the obtained exhaust gas temperature is not lower than 600° C. and lower than 700° C., 1.20 is obtained as the transition correction coefficient. When the obtained exhaust gas temperature is not lower than 700° C. and lower than 720° C., 1.20 is obtained as the transition correction coefficient. When the obtained exhaust gas temperature is not lower than 720° C. and lower than 740° C., 1.10 is obtained as the transition correction coefficient. When the obtained exhaust gas temperature is not lower than 740° C. and lower than 760° C., 1.10 is obtained as the transition correction coefficient. When the obtained exhaust gas temperature is not lower than 760° C. and lower than 800° C., 1.10 is obtained as the transition correction coefficient. When the obtained exhaust gas temperature is 800° C. or higher, 1.10 is obtained as the transition correction coefficient.

Subsequently, the CPU 11 stores the obtained transition correction coefficient in the RAM 13 (S26). Subsequently, the CPU 11 stores "1" in a memory area of the RAM 13 corresponding to the TransientFlg to thereby turn the TransientFlg ON (S27). Subsequently, the CPU 11 stores in the RAM 13 the present exhaust gas temperature obtained in S21 to thereby hold it (S28). After that, the CPU 11 ends the processing.

In the case where the CPU 11 determines in S23 that the exhaust gas temperature does not tend to increase (S23: NO), the CPU 11 determines whether or not the absolute value of the difference is not less than a second temperature (e.g., 30° C.) and the TransientFlg is OFF (S32). In the case where the absolute value of the difference is not less than the second temperature and the TransientFlg is OFF (S32: YES), with reference to a correction coefficient table which is shown in FIG. 6 and which is used when the exhaust gas temperature decreases, the CPU 11 obtains a correction coefficient for the target impedance transition, which coefficient corresponds to the present exhaust gas temperature obtained in S21 (S33). This correction coefficient table which is used when the exhaust gas temperature decreases is stored in the ROM 12. For example, when the exhaust gas temperature obtained from the exhaust gas temperature sensor 3 is not lower than 400° C. and lower than 500° C., 1.00 is obtained as the transition correction coefficient. When the obtained exhaust gas temperature is not lower than 500° C. and lower than 600° C., 1.00 is obtained as the transition correction coefficient. When the obtained exhaust gas temperature is not lower than 600° C. and lower than 700° C., 0.98 is obtained as the transition correction coefficient. When the obtained exhaust gas temperature is not lower than 700° C. and lower than 720° C., 0.96 is obtained as the transition correction coefficient. When the obtained exhaust gas temperature is not lower than 720° C. and lower than 740° C., 0.93 is obtained as the transition correction coefficient. When the obtained exhaust gas temperature is not lower than 740° C. and lower than 760° C., 0.90 is obtained as the transition correction coefficient. When the obtained exhaust gas temperature is not lower than 760° C. and lower than 800° C., 0.73 is obtained as the transition correction coefficient. When the obtained exhaust gas temperature is 800° C. or higher, 0.50 is obtained as the transition correction coefficient.

Subsequently, the CPU 11 stores the obtained transition correction coefficient in the RAM 13 (S34). Subsequently, the CPU 11 stores "1" in the memory area of the RAM 13 corresponding to the TransientFlg to thereby turn the TransientFlg ON (S35). Subsequently, the CPU 11 stores in the RAM 13 the present exhaust gas temperature obtained in S21 to thereby hold it (S28). After that, the CPU 11 ends the processing.

In the case where the CPU 11 has determined in S24 that the condition that the absolute value of the difference is not lower than the first temperature and the TransientFlg is OFF is not satisfied (S24: NO) (namely, the case where the absolute value of the difference is lower than the first temperature (e.g., 20° C.) or the case where the TransientFlg is ON and the transition period correction is presently performed (S24: NO)), when a state in which the absolute value of the difference is equal to or lower than a third temperature (e.g., 3° C.) continues for a predetermined period of time (e.g., 5 second) (S29: YES), the CPU 11 stores "0" in the memory area of the RAM 13 corresponding to the TransientFlg to thereby turn the TransientFlg OFF (S30). Subsequently, the CPU 11 sets the transition correction coefficient stored in the RAM 13 to 1.00 for initialization (S31). Subsequently, the CPU 11 stores in the RAM 13 the present exhaust gas temperature obtained in S21 to thereby hold it (S28). After that, the CPU 11 ends the processing.

Also, in the case where the CPU 11 has determined in S32 that the condition that the absolute value of the difference is not lower than the second temperature and the TransientFlg is OFF is not satisfied (S32: NO) (namely, in the case where the absolute value of the difference is lower than the second temperature (e.g., 30° C.) or the case where the TransientFlg is ON and the transition period correction is presently performed (S32: NO)), when a state in which the absolute value of the difference is equal to or lower than the third temperature (e.g., 3° C.) continues for the predetermined period of time (e.g., 5 second) (S36: YES), the CPU 11 stores "0" in the memory area of the RAM 13 corresponding to the TransientFlg to thereby turn the TransientFlg OFF (S37). Subsequently, the CPU 11 sets the transition correction coefficient stored in the RAM 13 to 1.00 for initialization (S38). Subsequently, the CPU 11 stores in the RAM 13 the present exhaust gas temperature obtained in S21 to thereby hold it (S28). After that, the CPU 11 ends the processing. Notably, in the case where the CPU 11 has made a NO determination in S29 and in the case where the CPU 11 has made a NO determination in S36, the CPU 11 stores in the RAM 13 the present exhaust gas temperature obtained in S21 to thereby hold it (S28). After that, the CPU 11 ends the processing.

Next, a method of correcting the target impedance TRi will be described. The CPU 11 reads out the transition correction coefficient stored in the RAM 13, and corrects the target impedance TRi in accordance with the following calculation formula.

$$TRi = TRi \times \text{transition correction coefficient}$$

As described above, such correction of the target impedance TRi is performed by the processing of S17 in the main processing program of FIG. 3.

Figure 7:
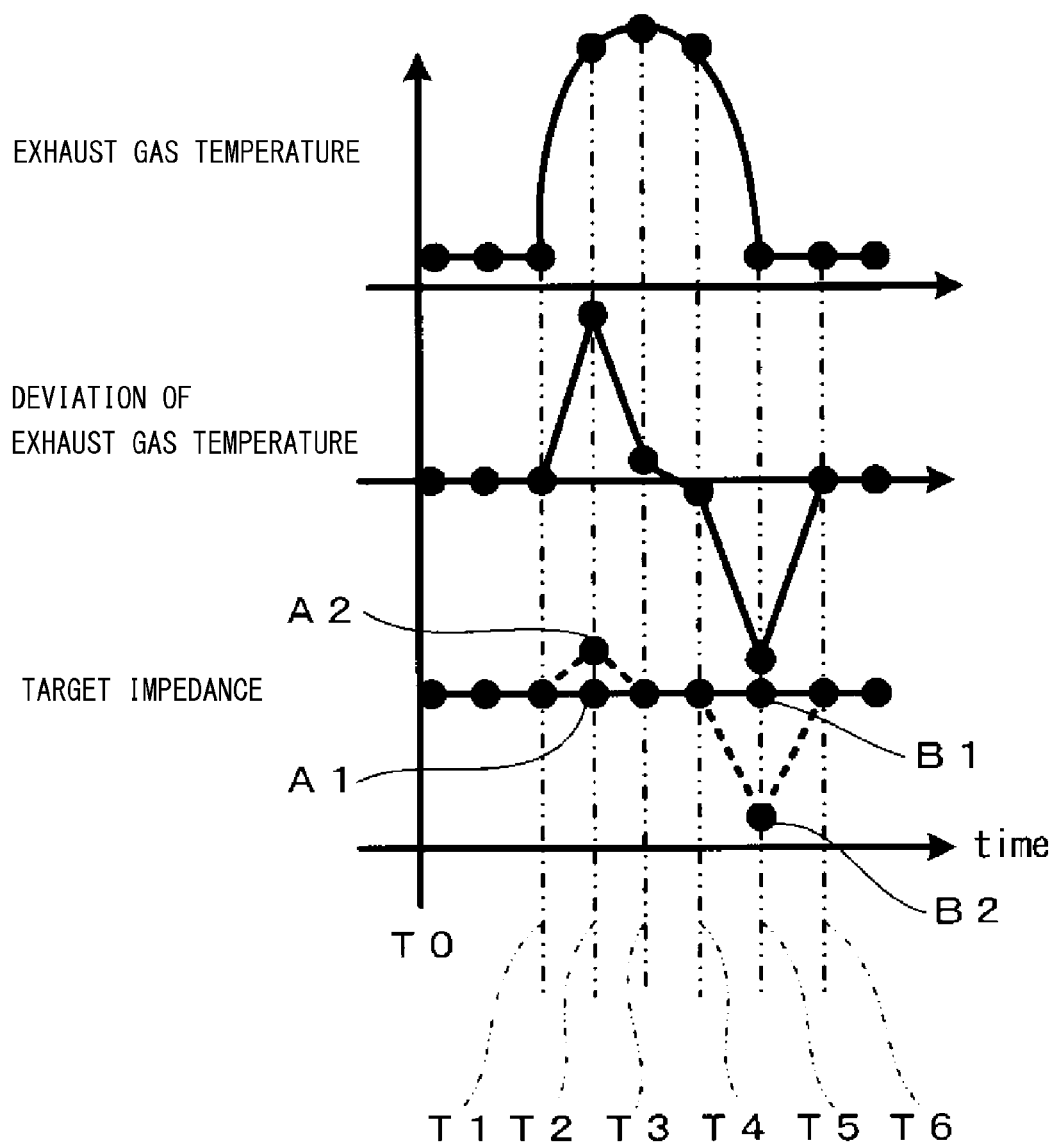
[FIG. 7] Graph showing changes in exhaust gas temperature, deviation of exhaust gas temperature, and target impedance.

The concept of the operation of the present embodiment will be described with reference to FIG. 7. It is to be noted that FIG. 7 is provided so as to facilitate the understanding of the concept of the operation of the ECU 5 as a sensor control apparatus. From timing T0 at which the engine 101 has started to timing T1, the exhaust gas temperature detected by the exhaust gas temperature sensor 3 is substantially stable without any change. In this period, since the deviation (change rate) of the exhaust gas temperature is 0, a predetermined target impedance is used without being corrected. The exhaust gas temperature increases sharply during the period between timing T1 and timing T2. Since the deviation (change rate) of the exhaust gas temperature increases in this period, the target impedance is corrected from A1 to A2. In a subsequent period between timing T2 and timing T3, since the increase in the exhaust gas temperature is slight, the deviation of the exhaust gas temperature decreases. Accordingly, the predetermined target impedance is used without being corrected. In a subsequent period between timing T3 and timing T4, since the exhaust gas temperature decreases slightly, the deviation of the exhaust gas temperature becomes slightly below zero (becomes negative). Accordingly, the predetermined target impedance is used without being corrected. In a subsequent period between timing T4 and timing T5, since the exhaust gas temperature decreases greatly, the deviation of the exhaust gas temperature assumes a large negative value. Accordingly, the target impedance is corrected from B1 to B2. In a subsequent period between timing T5 and timing T6, the exhaust gas temperature detected by the exhaust gas temperature sensor 3 does not change and is stable. Accordingly, in this period, the deviation of the exhaust gas temperature is 0. Accordingly, the predetermined target impedance is used without being corrected.

As described above, in the present embodiment, the CPU 11 of the ECU 5 reads the temperature of exhaust gas detected by the exhaust gas temperature sensor 3 at intervals of 1 second, and calculates the amount of change in the exhaust gas temperature in each interval of 1 second. In the case where the CPU 11 determines on the basis of the change amount that the engine 101 is in a transitional operation state, the CPU 11 corrects the target impedance. Namely, in the present embodiment, the determination as to whether or not the temperature change of the exhaust gas falls outside an allowable range is made by determining whether or not the change in the exhaust gas temperature detected by the exhaust gas temperature sensor 3 falls outside a specific range. When the temperature change of the exhaust gas is determined to fall outside the allowable range, the target impedance is corrected. Specifically, when the increase rate of the exhaust gas temperature is large, the target impedance is rendered larger than the default value by increasing the transition correction coefficient, whereby the heating by the heater 26 is restrained (the target heating temperature is lowered). Also, when the decrease rate of the exhaust gas temperature is large, the target impedance is rendered smaller than the default value by decreasing the transition correction coefficient, whereby the heating by the heater 26 is enhanced (the target heating temperature is elevated). Accordingly, even when the engine 101 is in a transitional operation state, the cell 21 (detection element) of the oxygen sensor 2 can be accurately controlled to the target heating temperature, whereby accurate detection of oxygen concentration can be continued.

In the above-described embodiment, the engine 101 is an example of the "internal combustion engine"; the ECU 5 is an example of the "sensor control apparatus"; and the oxygen sensor 2 is an example of the "gas sensor." The exhaust gas temperature sensor 3 is an example of the "exhaust gas temperature sensor"; and the heater 26 is an example of the "heater." The CPU 11 which executes the processing of S16 of FIG. 3 is an example of the "element impedance detection means"; and the heater control circuit 50 and the CPU 11 which executes the processing of S17 of FIG. 3 is an example of the "heater-supplied-power control means." The CPU 11 which executes the determination processing of S24 or S32 of FIG. 4 is an example of the "temperature change determination means"; the CPU 11 which executes the processing of S25 or S33 of FIG. 4 is an example of the "correction means"; and the CPU 11 which executes the determination processing of S29 or S36 of FIG. 4 is an example of the "time determination means."

The present invention is not limited to the above-described embodiment, and various modifications are possible. For example, the first temperature in S24 of FIG. 4 is not necessarily required to be 20° C., and the first temperature may be 10° C. Similarly, the second temperature in S32 of FIG. 4 is not necessarily required to be 30° C., and the second temperature may be 10° C. or 20° C. Similarly, the third temperature in S29 and S36 of FIG. 4 is not necessarily required to be 3° C., and the third temperature may be 5° C., etc. The predetermined period is not necessarily required to be 5 seconds, and the predetermined period may be 10 seconds, etc. That is, these values may be adequately determined in accordance with the characteristics of the engine 101 and the oxygen sensor 2. The transition period correction of FIG. 4 is not necessarily required to be performed at intervals of 1 second, and may be performed at shorter intervals.

In the above-described embodiment, in order to determine whether or not the temperature change of the exhaust gas is that in the transition period in which the operation state of the internal combustion engine changes, the exhaust gas temperature is detected through use of the exhaust gas temperature sensor 3, and a determination is made as to whether the absolute value of the deviation is equal to or higher than the first temperature (S24) or as to whether the absolute value of the deviation is equal to or higher than the second temperature (S32). However, when a determination is made as to whether the temperature change of the exhaust gas falls outside the allowable range, instead of measuring the temperature of the exhaust gas using the exhaust gas temperature sensor 3, the temperature of the exhaust gas may be estimated from the operation state of the engine 101.

For example, a characteristic map defining the relation between the exhaust gas temperature and the operation state of the engine 101 is previously stored in the ROM 12 of the microcomputer 10 of the ECU 5. Various parameters for determining the operation state, such as engine rotation speed, width of fuel injection pulses, and throttle opening, are input to the microcomputer 10. The CPU 11 of the microcomputer 10 calculates the operation state of the engine 101, estimates the exhaust gas temperature with reference to the above-mentioned characteristic map, calculates the difference between the estimated exhaust gas temperature and the exhaust gas temperature estimated in the previous computation cycle, and calculates the temperature change of the exhaust gas. Alternatively, as disclosed in Japanese Patent Application Laid-Open (kokai) No 2010-7492, the temperature of exhaust gas may be estimated by correcting a previously set reference exhaust gas temperature by correction coefficients determined on the basis of the indicated power in an operation state of the engine 101 and an intake air quantity ratio, which is the ratio of an intake air quantity in the operation state of the engine 101 to a reference intake air quantity corresponding to the operation state of the engine 101.

DESCRIPTION OF REFERENCE NUMERALS

2: oxygen sensor (gas sensor)
3: exhaust gas temperature sensor
5: electronic control unit (ECU)
10: microcomputer
11: CPU
12: ROM
13: RAM
20: output detection circuit
21: cell
26: heater
30: pulse input circuit
50: heater control circuit

The invention claimed is:

1. A sensor control apparatus connected to a gas sensor which is attached to an exhaust pipe of an internal combustion engine and which includes a detection element for detecting the concentration of a gas contained in exhaust gas and a heater for heating the detection element, comprising:
   element impedance detection means for detecting an impedance of the detection element;
   heater-supplied-power control means for feedback-controlling power supplied to the heater such that the element impedance detected by the element impedance detection means coincides with a target impedance;
   temperature change determination means for determining whether or not a change in the temperature of exhaust gas flowing through the exhaust pipe falls outside a previously set allowable range; and
   correction means for correcting the target impedance when the temperature change determination means determines that the change in the temperature of the exhaust gas falls outside the allowable range,
   wherein the correction means corrects the target impedance by multiplying the target impedance by a correction coefficient, and changes the correction coefficient on the basis of the temperature of the exhaust gas at the time of start of a change in the temperature of the exhaust gas, which change has deviated from the allowable range.

2. A sensor control apparatus as claimed in claim 1, wherein the temperature change determination means determines whether or not the change in the temperature of the exhaust gas falls outside the allowable range by determining whether or not a change in an output value of an exhaust gas temperature sensor attached to the exhaust pipe and detecting the temperature of the exhaust gas falls outside a specific range.

3. A sensor control apparatus as claimed in claim 2, wherein the specific range is the range of a change in the output value corresponding to 10° C. or greater per sec.

4. A sensor control apparatus as claimed in claim 2, further comprising time determination means for determining whether or not a state in which the difference between output values of the exhaust gas temperature sensor obtained at predetermined time intervals is equal to or lower than a specific temperature has continued for a predetermined period of time, wherein
the correction means stops the correction of the target impedance when the time determination means determines that the state in which the difference between output values of the exhaust gas temperature sensor obtained at the predetermined time intervals is equal to or lower than the predetermined value has continued for the predetermined period of time.

5. A sensor control apparatus as claimed in claim 2, wherein the correction means corrects the target impedance when the output value of the exhaust gas temperature sensor indicates that the temperature of the exhaust gas is increasing and the temperature change determination means determines that the change in the output value falls outside the specific range.

6. A sensor control apparatus as claimed in claim 2, wherein the correction means corrects the target impedance when the output value of the exhaust gas temperature sensor indicates that the temperature of the exhaust gas is decreasing and the temperature change determination means determines that the change in the output value falls outside the specific range.

7. A sensor control system comprising the gas sensor and the sensor control apparatus as claimed in claim 6 connected to the gas sensor.

8. A sensor control apparatus connected to a gas sensor which is attached to an exhaust pipe of an internal combustion engine and which includes a detection element for detecting the concentration of a gas contained in exhaust gas and a heater for heating the detection element, comprising:
    element impedance detection means for detecting an impedance of the detection element;
    heater-supplied-power control means for feedback-controlling power supplied to the heater such that the element impedance detected by the element impedance detection means coincides with a target impedance;
    temperature change determination means for determining whether or not a change in the temperature of exhaust gas flowing through the exhaust pipe falls outside a previously set allowable range; and
    correction means for correcting the target impedance when the temperature change determination means determines that the change in the temperature of the exhaust gas falls outside the allowable range,
    wherein the temperature change determination means determines whether or not the change in the temperature of the exhaust gas falls outside the allowable range by determining whether or not a change in an output value of an exhaust gas temperature sensor attached to the exhaust pipe and detecting the temperature of the exhaust gas falls outside a specific range; and
    said sensor control apparatus further comprising time determination means for determining whether or not a state in which the difference between output values of the exhaust gas temperature sensor obtained at predetermined time intervals is equal to or lower than a specific temperature has continued for a predetermined period of time, wherein
    the correction means stops the correction of the target impedance when the time determination means determines that the state in which the difference between output values of the exhaust gas temperature sensor obtained at the predetermined time intervals is equal to or lower than the predetermined value has continued for the predetermined period of time.

* * * * *